United States Patent
Crawford et al.

(10) Patent No.: US 7,591,716 B2
(45) Date of Patent: Sep. 22, 2009

(54) PRODUCING NOTCH FEATURE IN SMALL DIAMETER STEEL ALLOY NEEDLE WIRE

(75) Inventors: William A. Crawford, Cincinnati, OH (US); Kenneth V. Moran, Loveland, OH (US); Terry A. McFarland, Burlington, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 482 days.

(21) Appl. No.: 11/445,469

(22) Filed: Jun. 2, 2006

(65) Prior Publication Data
US 2007/0277363 A1  Dec. 6, 2007

(51) Int. Cl.
*B24B 41/06* (2006.01)
(52) U.S. Cl. .................. 451/365; 451/369; 451/382; 451/908; 269/47; 606/167; 606/223
(58) Field of Classification Search .......... 451/182, 451/231, 364, 365, 369, 382, 908; 269/47; 606/167, 185, 222, 223; 205/663; 310/216
See application file for complete search history.

(56) References Cited
U.S. PATENT DOCUMENTS

| | | | | |
|---|---|---|---|---|
| 3,789,478 A | * | 2/1974 | Stenger | 193/27 |
| 4,216,628 A | * | 8/1980 | Wada | 451/232 |
| 5,476,480 A | * | 12/1995 | Matsutani et al. | 606/222 |
| 6,018,860 A | * | 2/2000 | Smith et al. | 29/558 |
| 6,322,581 B1 | * | 11/2001 | Fukuda et al. | 606/223 |

* cited by examiner

*Primary Examiner*—Eileen P. Morgan
(74) *Attorney, Agent, or Firm*—Welsh & Flaxman LLC

(57) ABSTRACT

A notch-locating fixture for forming notches at predetermined locations along a needle wire used in a surgical suturing apparatus includes a base having at least one semi-circular recess shaped and dimensioned for receiving the needle wire. The fixture also includes a cover member including at least one aligned slot formed therein in a manner providing a grinding wheel with access to needle wire held between the base and the cover member. The fixture further includes a securing structure selectively coupling the base to the cover member.

12 Claims, 7 Drawing Sheets

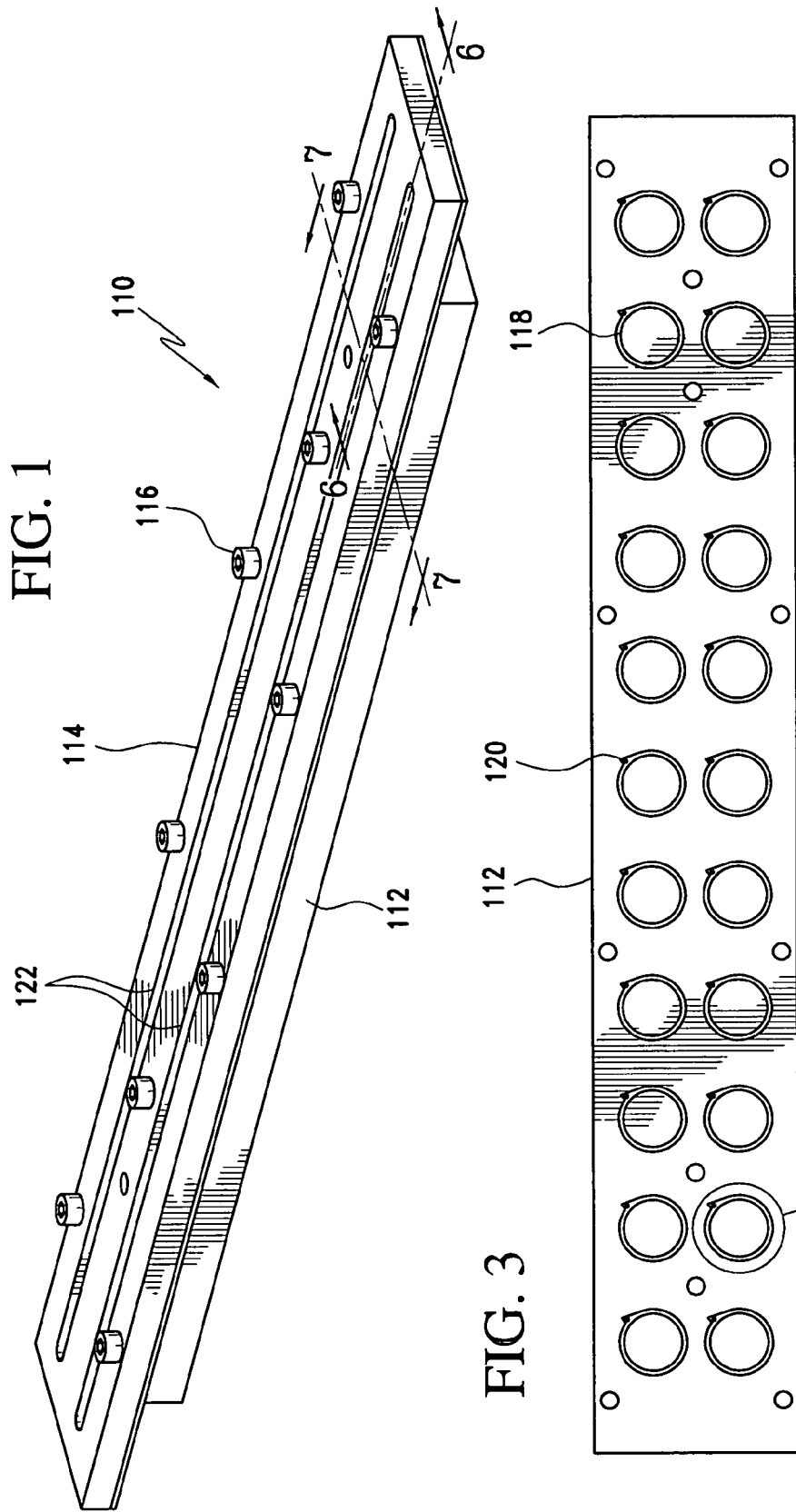

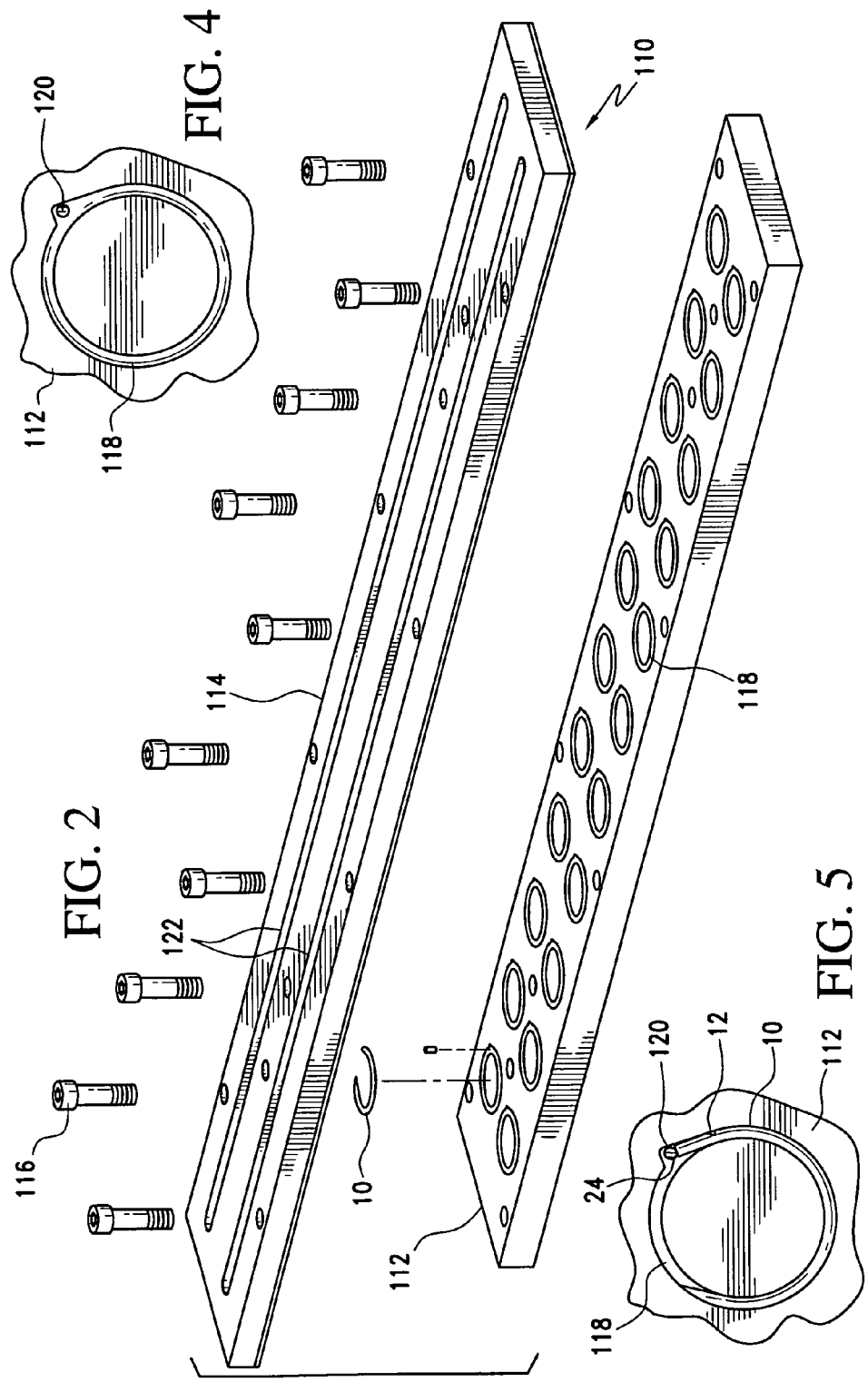

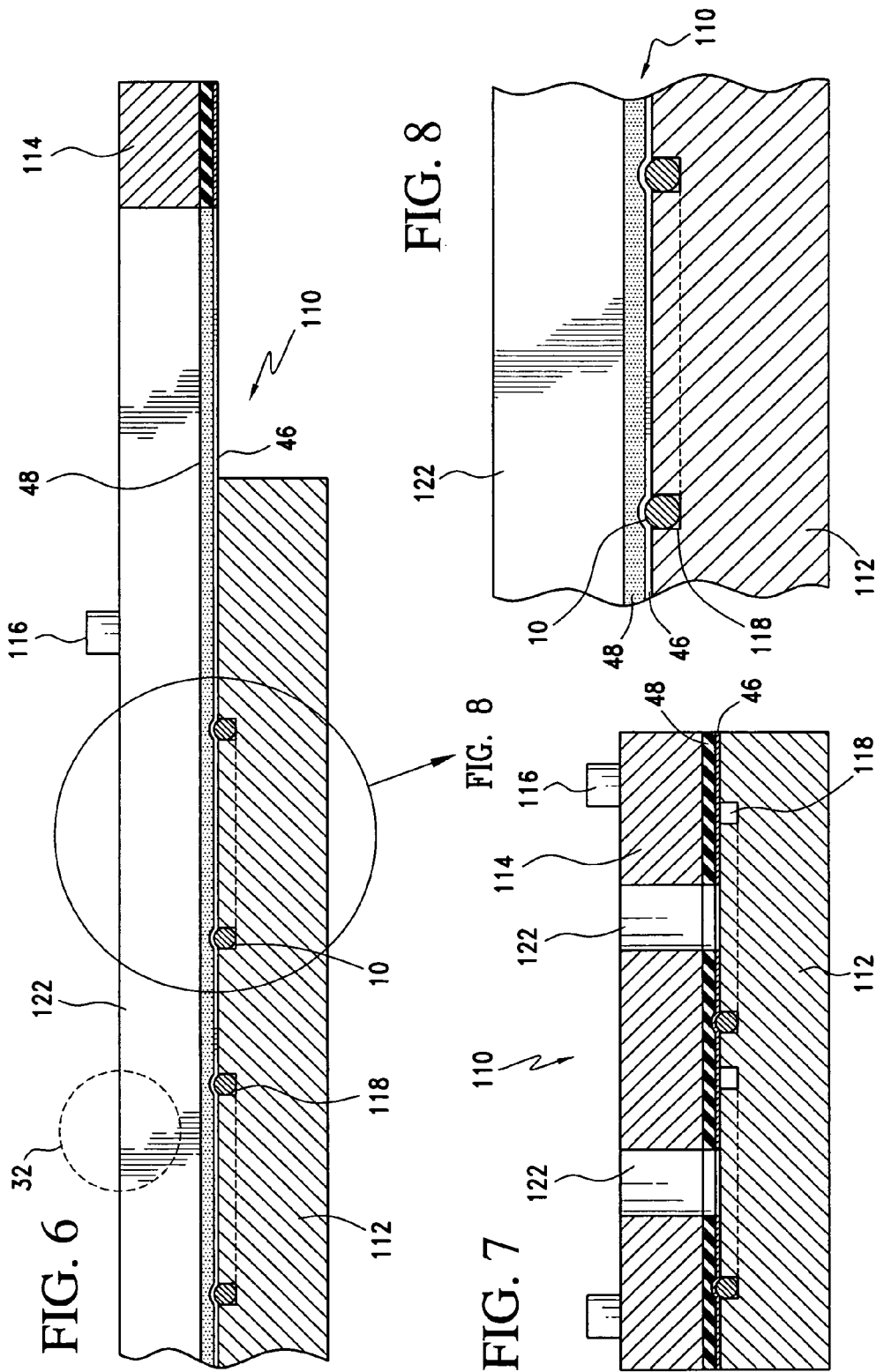

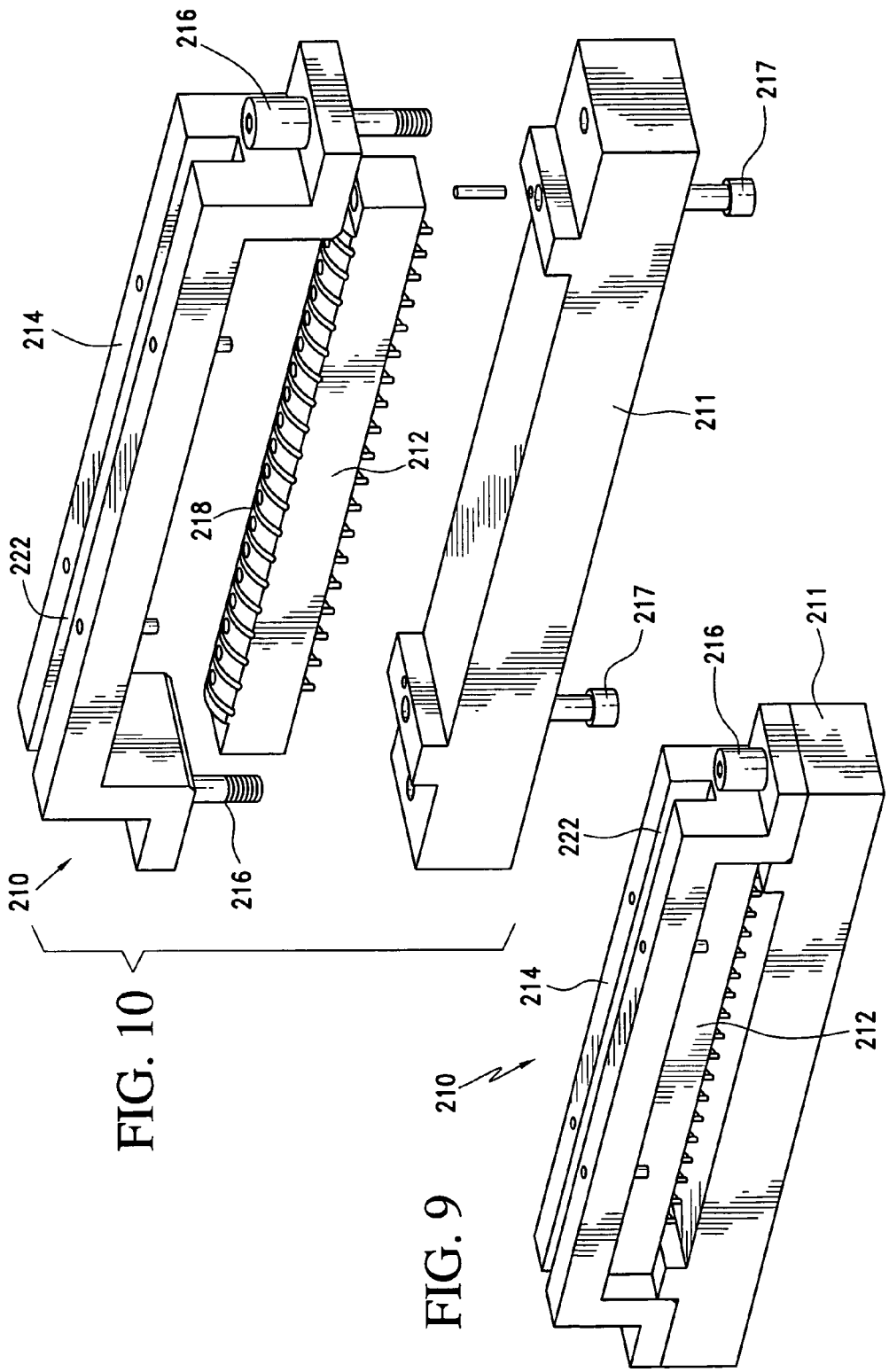

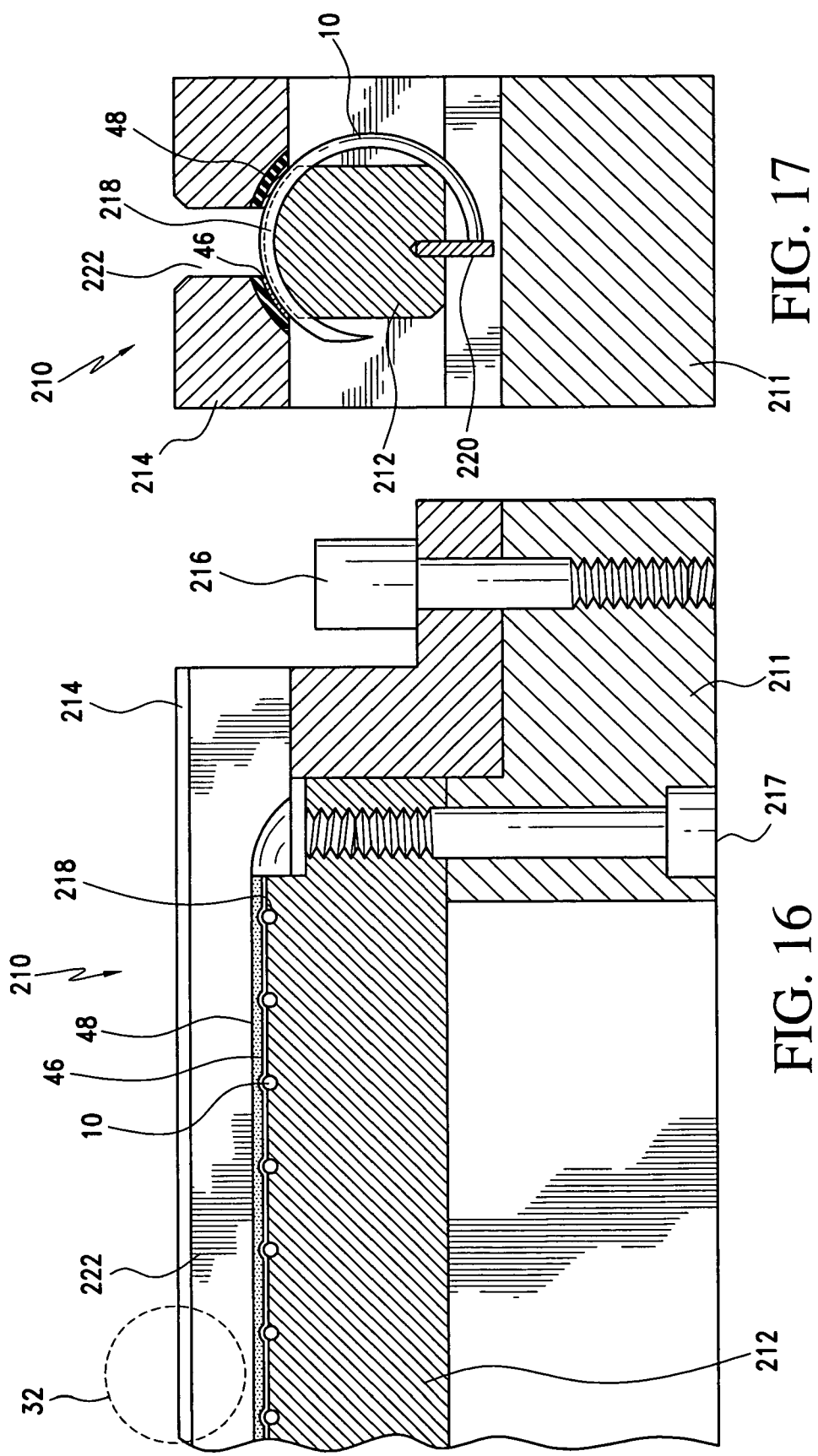

PRODUCING NOTCH FEATURE IN SMALL DIAMETER STEEL ALLOY NEEDLE WIRE

BACKGROUND OF THE INVENTION

1. Field of the Invention

The invention relates to the manufacture of small diameter needle wire for use in the manufacture of medical instruments, for example, endoscopic suturing apparatuses. In particular, the invention relates to a method and apparatus for creating notches in small diameter steel alloy needle wire for use in the manufacture of endoscopic suturing apparatuses.

2. Description of the Prior Art

The recent development of continuous endoscopic suturing devices, such as those disclosed in commonly owned U.S. patent application Ser. No. 11/394,163, entitled "SURGICAL SUTURING APPARATUS WITH COLLAPSIBLE CHAMBER", which is incorporated herein by reference, has necessitated the development of curved needles. As those skilled in the art will certainly appreciate, these needles continuously move through a loop as they pass sutures in and out of tissue. In order to ensure the needles do in fact continuously loop through a circular path, it is necessary that the needles be manufactured to very high tolerances.

The needles used in these suturing apparatuses are commonly produced of small diameter steel alloy needle wire. Some suturing apparatuses require that notches be cut along the needle wire. As those skilled in the art will certainly appreciate, the formation of appropriate notches at the ends of small diameter needle wire and the curvature of the small diameter needle wire, for example, wire having a diameter of less than 0.100", is very difficult. In fact, notch production for utilization in conjunction with medical instruments requires that the needle wire cannot be deformed in any way by the notching process, the mechanical properties of the basic wire materials cannot be altered by the notching process and/or the metallurgical properties of the wire cannot be altered by the notching process. Similarly, usage in the manufacture of suturing apparatuses requires that the curvature of the needles can not vary or the needles will not function properly when placed within the suturing apparatus and required to rotate in a continuous loop of a predefined diameter.

All of these difficulties are compounded by the small diameter of the needle wire. The small diameter is necessitated by the small diameter loops through which the needles must pass when used in accordance with the designs of endoscopic suturing devices. In particular, designers of these suturing devices are continuously striving to reduce the profile of the suturing devices. One limiting factor in the reduction of the profile of these endoscopic suturing devices is the diameter of the loop through which the needle must rotate in the application of a suture. The smaller the potential diameter, the smaller the profile of the suturing device may be (that is, so long as the remaining components are designed to work in conjunction with the reduced diameter path of the suturing needle).

With the foregoing in mind, it is very difficult to consistently and effectively form notches in small diameter needle wire for suturing needles used in the production of endoscopic suturing devices. A need, therefore, exists for a method and apparatus which provides a convenient, reliable and cost effective manner for producing notches in small diameter steel alloy needle wires. The present invention provides such a method and apparatus.

SUMMARY OF THE INVENTION

It is, therefore, an object of the present invention to provide a notch-locating fixture for forming notches at predetermined locations along a needle wire used in a surgical suturing apparatus. The fixture includes a base having at least one semi-circular recess shaped and dimensioned for receiving the needle wire. The fixture also includes a cover member including at least one aligned slot formed therein in a manner providing a grinding wheel with access to needle wire held between the base and the cover member. The fixture further includes a securing structure selectively coupling the base to the cover member.

It is also an object of the present invention to provide a fixture wherein the securing structure is a plurality of bolts.

It is also another object of the present invention to provide a fixture wherein the base includes a plurality of semi-circular recesses.

It is also a further object of the present invention to provide a fixture wherein the at least one semi-circular recess includes an alignment abutment shaped and dimensioned for engaging a blunt end of the needle wire.

It is another object of the present invention to provide a fixture wherein the recess includes a width which is approximately 5% larger than that of the needle wire.

It is a further object of the present invention to provide a fixture wherein the aligned slot is oriented in a manner creating notches along a side of the needle wire.

It is also an object of the present invention to provide a fixture wherein the aligned slot is oriented in a manner creating notches along an exterior circumference of the needle wire.

It is still another object of the present invention to provide a fixture wherein the base is a central rod.

It is yet a further object of the present invention to provide a fixture including a thin piece of a conductive sheet positioned between the needle wire and the cover member.

It is also an object of the present invention to provide a fixture wherein the conductive sheet is a stainless steel sheet.

It is also another object of the present invention to provide a fixture further including a foam pad positioned between the conductive sheet and the cover member.

It is also a further object of the present invention to provide a fixture wherein the foam pad is a neoprene closed cell foam pad.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a perspective view of a notch-locating fixture in accordance with a first embodiment of the present invention.

FIG. 2 is an exploded view of the fixture shown in FIG. 1.

FIG. 3 is a top plan view of the base of the fixture shown in FIG. 1.

FIG. 4 is a detailed view of a recess formed in the base without a needle wire positioned therein.

FIG. 5 is a detailed view of a recess formed in the base with a needle wire positioned therein.

FIGS. 6, 7 and 8 are respectively cross sectional views of the fixture shown in FIG. 1.

FIG. 9 is a perspective view of a notch-locating fixture in accordance with a second embodiment of the present invention.

FIG. 10 is an exploded view of the notch-locating fixture shown in FIG. 9 without needle wires.

FIGS. 14, 15, 16 and 17 are various cross sectional views of the embodiment shown in FIG. 9.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

Figure 11:
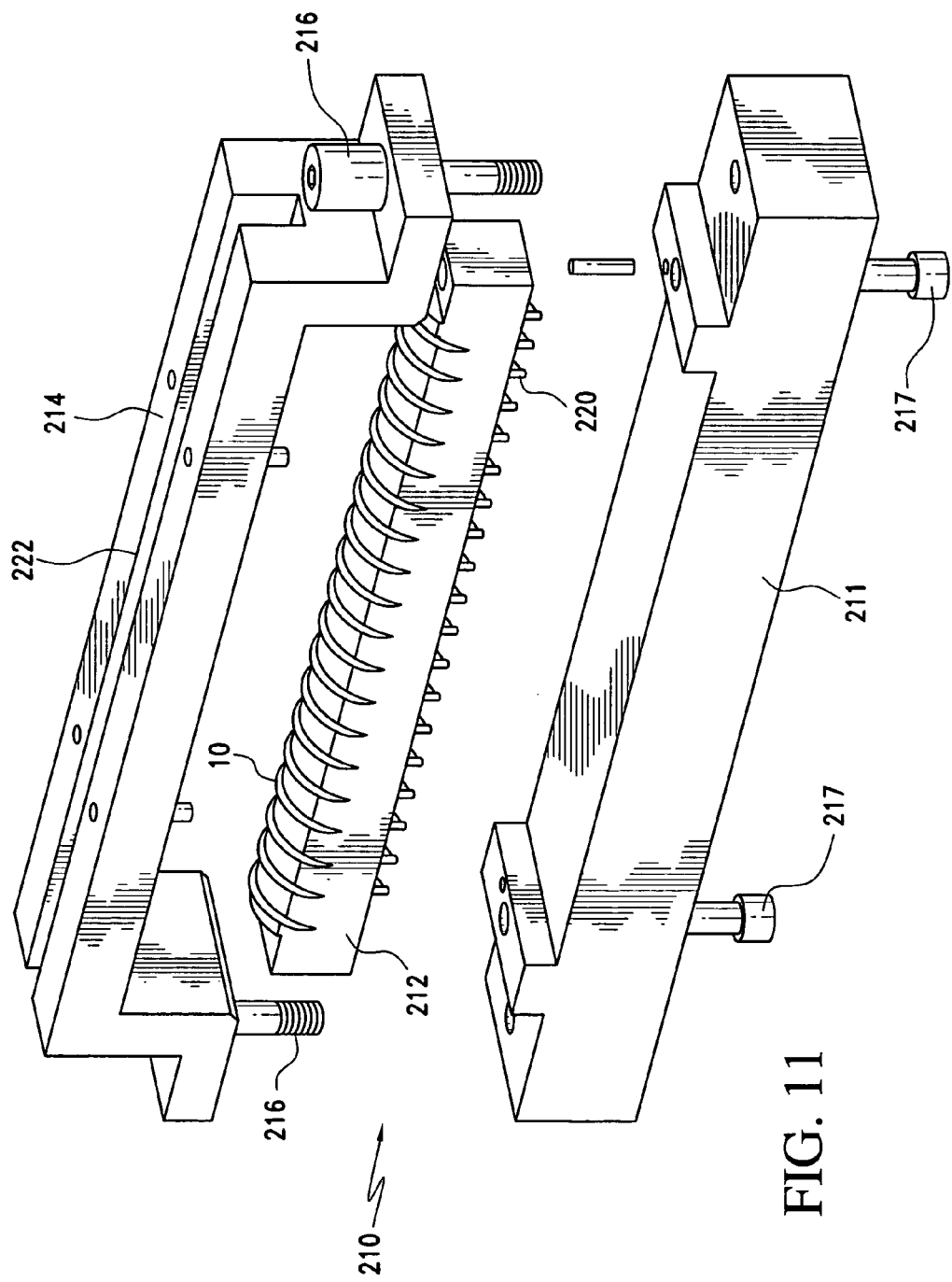
FIG. 11 is an exploded view with needle wires.
Figure 12:
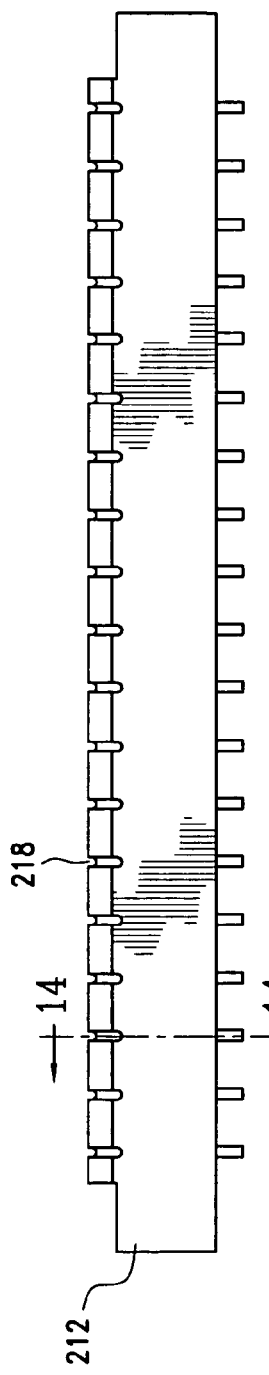
FIGS. 12 and 13 are respective side and top plan views of the central rod of the fixture.
Figure 13:
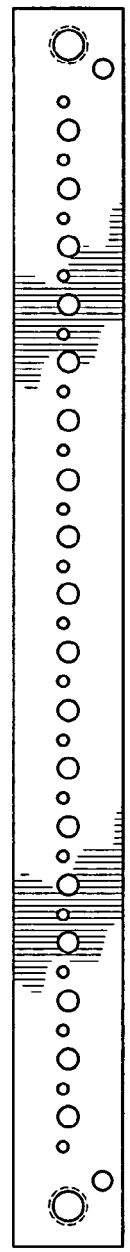
Figure 14:
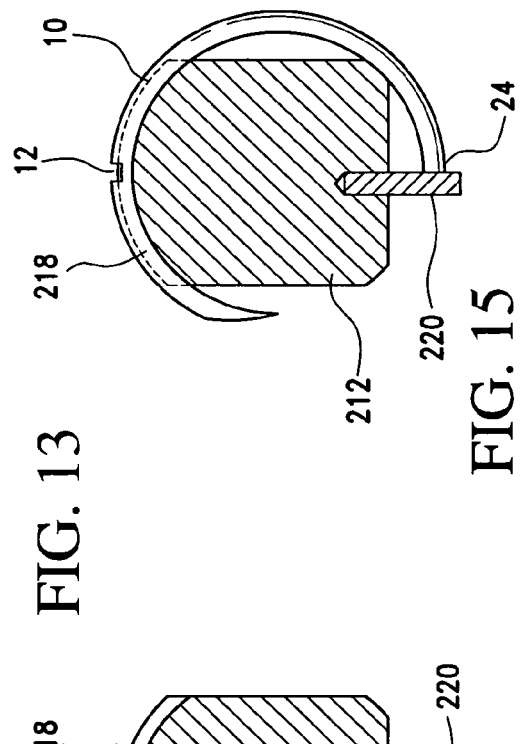
Figure 15:
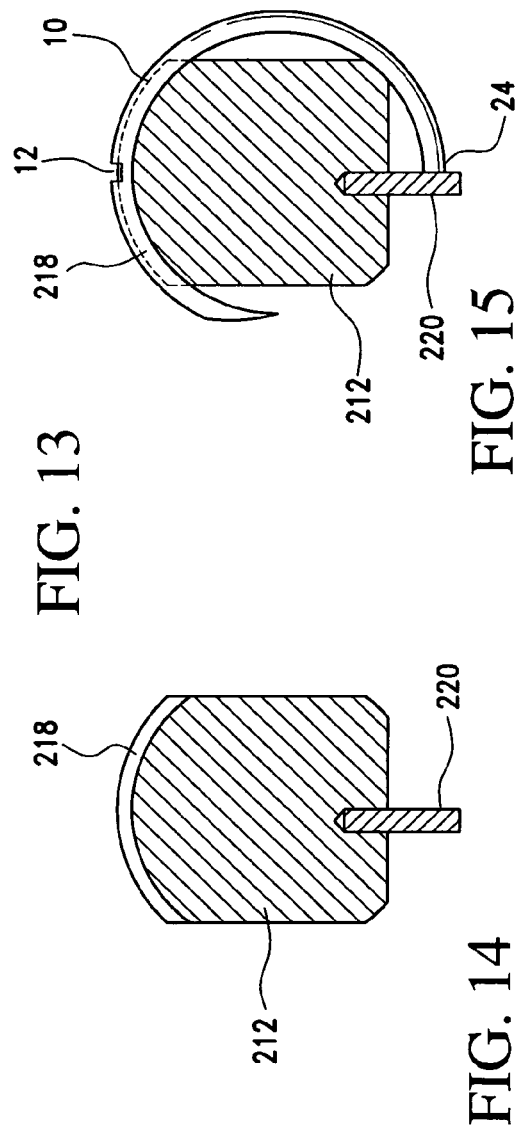

With reference to the various figures, a small diameter alloy steel needle wire 10 is disclosed. The needle wire 10 is produced with a predetermined radius of curvature and includes a notch 12 machined at an end thereof in accordance with a preferred embodiment of the present invention. The notch 12 is created at a predetermined location along the arc defined by the needle 10 as required by the actuation mechanism of the suturing apparatus 14 for which the needle wire 10 is designed. The notch 12 may be produced along the side of the needle wire 10 or along the outer circumference of the needle wire 10. With this in mind, the present invention discloses two notch-locating fixtures 110, 210; one for use in creating side oriented notches (see FIGS. 1 to 8) and another for forming notches along the outer circumference (see FIGS. 9 to 17).

The term small diameter needle wire is used throughout the body of the present disclosure. This term small diameter needle wire is meant to refer to alloy steel needle wires having a diameter of less than 0.100" diameter. While alloy steel needle wires are used in accordance with a preferred embodiment of the present invention, other materials could be used without departing from the spirit of the present invention. However, any materials used must be capable of conducting electricity so that notches may be ground in accordance with the present invention as discussed below in greater detail.

It is imperative the formation of the notch 12 not alter the needle wire 10 in that the needle wire 10 must retain its strength and smoothness characteristics such that it may be effectively used in conjunction with an endoscopic suturing apparatus as discussed above. The present notch forming process and associated apparatus are capable of producing notches 12 within small diameter needle wires 10 wherein the wire is not deformed in any way by the notching process, the mechanical properties of the basic needle wire material are not altered by the notching process and the metallurgical properties of the wire are not altered by the notching process. In addition, the present process is capable of notching small diameter needle wires 10 wherein the notching process yields mass production quantities of notched needle wire parts and the notch 12 geometry is held to precise dimensional requirements.

In particular, and in accordance with a preferred embodiment of the present invention, notches 12 exhibit precise notch geometry angles of +/−2 degrees with a process Cpk of 1.33, or greater, precise depth to within 0.005" with a process Cpk of 1.33, or greater, and bottom of notch radius of 0.009" maximum. In addition, the profile positional location of the notch 12 features on the needle wire 10 are maintained to within 0.010" and perpendicularity to within 0.005" both with a process Cpk of 1.33, or greater.

It is important that the needle wire 10 be held in a predetermined orientation for creation of the notches 12 as required in accordance with the present invention. With this in mind, needle wire 10 which has been preformed with the desired radius of curvature may be notched in a first notch-locating fixture 110 shaped and dimensioned such that each processed needle wire 10 is produced with an identical radius of curvature and an identical side oriented notch. Similarly, each preformed needle wire 10 may be notched in a second notch-locating fixture 210 such that they are held in exactly the same manner so that exactly the same outer circumference notch 12 may be cut in each of the needle wires 10.

More particularly, the first notch-locating fixture 110 includes base 112 and a cover member 114. The cover member 114 is secured to the base 112 using a series of bolts 116 to secure it thereto. The base 114 includes a semi-circular recess 118 shaped and dimensioned to receive and locate the needle wire 10. In fact, the first notch-locating fixture 110 includes a series of circumferential recesses 118 shaped and dimensioned for supporting the curved needle wires 10 therein. A plurality of aligned, identical semi-circular recesses 118 are provided such that the needle wires 10 may be mass produced in an efficient manner. Although only one of the semi-circular recesses 118 is disclosed below, those skilled in the art will appreciate that the recesses 118 are all identical and the present description applies equally to each of the recesses 118 provided in the first notch-locating fixture 110.

The semi-circular recess 118 includes an alignment abutment 120 along one side of the recess 118. The alignment abutment 120 is the point at which the blunt end 24 (that is, the rear end) of the needle wire 10 is positioned. In this way, everything else may be measured from the blunt end 24 of the needle wire 10 such that a notch 12 is produced exactly a specified distance, for example, 180 degrees, from the blunt end 24 of the needle wire 10. The specific channel width and radius of the series of circumferential recesses 118 of notch-locating fixture 110 ensures that each needle wire 10 is located to exactly the same radius of curvature by considering both the thickness of the wire and the spring back inherent in all steel needle wire when it is released from the notch locating fixture 110.

In particular, and accounting for the mechanical physical phenomena of bending any wire, compression (inside of wire curve axis) and tension forces (outside of wire curve axis) do not perfectly cancel in the column of wire. Therefore, the curve is not actually a perfect continuous curve as visually presented, but is actually a series of small discontinuous straight sections connected by local bent sections. As such, an average roundness ratio of 15.9 to 1 (curve diameter to small wire diameter) results in an average roundness of 0.4% or about 0.004".

With this in mind, the width of the recess 118 is only 5% larger than the small wire 10 diameter and whose radius is also 5% larger than the centerline of the bend radius of the produced needle wire 10, or 45% of the diameter of the needle wire 10, measured from the average inside produced diameter of the needle wire 10. This is unique in that if the recess 118 to needle wire 10 clearance is larger than 5% the needle wire 10 will not be repeatably located in the recess 118 and therefore the notch 12 position locations cannot be achieved to the precision required. Conversely, if the recess 118 is less than this ratio the small needle wire 10 will not fit into the recess 118 taking into account its natural average roundness resulting from bending to the curve shape.

As briefly mentioned above, the first notch-locating fixture 110 is provided with a cover member 114 which is secured and clamped to the base 112 via bolts 116, with the needle wire 10 being held therebetween with the respective recesses 118. Although bolts are disclosed in accordance with a preferred embodiment of the present invention, it is contemplated other securing structures, for example, Bellville, compression, or torsional spring(s), may also be used without departing from the spirit of the present invention. As such, the base 112, cover member 114, and recesses 118 serve to capture, locate and hold the already curved needle wire 10 in a statically consistent and accurate manner to facilitate Electro-Chemical Grinding of the notches 12 along a side of a curved needle wire 10. Access to the needle wires 10 for grinding via a grinding wheel 32 discussed below in greater detail is provided by aligned slots 122 formed within the cover member 114. The slots 122 are aligned to provide the grinding wheel 32 with access to a predetermined section of each needle wire 10 so as to facilitate consistent notch formation. In particular, the aligned slot 122 is oriented in a manner allowing clearance for an electro-chemical grinding wheel 32 to create notches along a side of the needle wire 10.

Where it is desired to notch the needle wire 10 along its outer circumference, a second notch-locating fixture 210 may be employed. As with the first notch-locating fixture 110, the second notch-locating fixture 220 includes a central rod 212 upon which a series of needle wires 10 are supported. The needle wires 10 are supported in identical configurations such that a notch 12 will be cut at specific predetermined locations along the arc of the needle wire 10 relative to the blunt end 24 of the needle wire 10.

More particularly, the central rod 210 includes a series of circumferential recesses 218 shaped and dimensioned for supporting the curved needle wires 10 therein. As with the recesses 218 of the first notch-locating fixture 110, a plurality of semi-circular recesses 218 are provided such that the needle wires 10 may be mass produced in an efficient manner. Although only one of the semi-circular recesses 218 is disclosed below, those skilled in the art will appreciate that the recesses 218 are all identical and the present description applies equally to each of the recesses 218 provided in the notch-locating fixture 210.

The semi-circular recess 218 includes an alignment abutment 220 along the lower side of the recess 26. As with the first notch-locating fixture 110, the alignment abutment 220 is the point at which the blunt end 24 (that is, the rear end) of the needle wire 10 is positioned. In this way, everything else may be measured from the blunt end 24 of the needle wire 10 such that a notch 12 is produced exactly a specified distance, for example, 180 degrees, from the blunt end 24 of the needle wire 10.

The notch-locating fixture 210 includes a cover member 214 which engages the upper surface of the needles 10 to hold them in place as the grinding wheel 32 passes thereacross. The cover member 214 is secured to the top of the central rod 212 via bolts 216, thereby placing the central rod 212 and the needle wires 10 positioned thereon between the base 211 upon which the central rod 212 is supported and the cover member 214. Secondary bolts 217 are used in securing the base 211 to the central rod 212 for proper alignment thereof. The cover member 214 further includes a slot 222 aligned with the central rod 212 providing the grinding wheel 32 with access to the various needle wires 10 supported upon the central rod 212. As with the prior embodiment, the slot 222 is oriented in a manner allowing clearance for an electro-chemical grinding wheel 32 to create notches along a side of the needle wire 10.

As will be appreciated based upon the following disclosure, the electro-chemical grinding process in accordance with the present invention, and as used in conjunction with both the first and second notch-locating fixtures 110, 210, is unique from other metal removal processes in that the metal to be removed to create the notch 12 geometry is not removed mechanically, but rather electro-chemically. As such the grinding wheel 32, dressed to the geometry configuration of the notch 12 to be produced, never actually touches the needle wire 10. In this way the present process meets the small needle wire requirement of not mechanically altering or deforming the part since there is no friction generated and thus no deforming pressure or metallurgicaly altering heat generated in the electro-chemical grinding process.

In accordance with the present invention, the hardened temper of the small needle wire 10 simply must be maintained in the local area of the notch 12. The metal ionizing heat generated by the electrical process is carried away in the material removed by the high pressure fluid flow of the chemical electrolyte solution which acts as an insulator between the positively electrically charged wire part (the cathode) and the negatively charged grinding wheel (the anode). The electro-chemical grinding process is also very fast, capable of removing especially small amounts of material very quickly. In this way, the electro-chemical grinding process overcomes the traditional disadvantage of conventional grinding by precisely controlling the flow of the electrical current between the small needle wire 10, the grinding wheel 32, and either the first or second notch-locating fixture 110, 210. The flow of electrical current and electrolyte removing the material must be precisely controlled to produce acceptable finished geometry of the notch 12 in the small needle wire 10.

The electro-chemical grinding process in accordance with the present invention is used to produce notches 12 in small needle wire 10 using the following optimized components: a grinding wheel 32, the first or second notch-locating fixture 110, 210 for the needle wire part for presentation to the grinding wheel 32 and a guiding mechanism for controlling the path of the grinding wheel to successfully produce the notch geometry. In accordance with a preferred embodiment, a commercially available 3-axis Computerized Numerical Control (CNC) Electo-Chemical Grinding Machine (ECG) with $4^{th}$ axis rotary positioning is employed.

With regard to the grinding wheel 32 configuration, it is preferably a Cubic Boron Nitrate (CBN) or Diamond coated copper electro-chemical grinding wheel. The grinding wheel 32 must have a particle size not to exceed 0.004" average diameter. The grinding wheel 32 in accordance with a preferred embodiment of the present invention is precisely dressed using a diamond dressing point so that exactly one grain is tangent to the two sides at the point of the notch. In accordance with a preferred embodiment, the wheel is dressed conventionally by successive strokes of the diamond dressing point across and perpendicular to the face of the rotating grinding wheel, with either the diamond point or the wheel advancing a very small incremental distance with each stroke causing grains of the wheel to be dislodged.

Specifically, a 140-grit or finer electro-chemical grinding wheel 32 is required. Such a grinding wheel 32 will produce a 0.005" diameter radius in the bottom of the notch 12. This configuration will produce the required 0.009" maximum radius required until the grains are lost from the grinding wheel 32 through wear.

Subsequent re-dressing of the grinding wheel 32 is required to maintain the required notch 12 geometry. In accordance with a preferred embodiment of the present invention, it is contemplated, and determined empirically, that the number of notch cuts between wheel dressings will be approximately 400 notches.

With regard to the first and second notch-locating fixtures 110, 210, the needle wire 10 parts are located for grinding by an electrically conductive steel tool fixture as shown in the various figures. As discussed above, the first notch-locating fixture 110 includes recesses 118 and the second notch-locating fixture 210 includes a perpendicularly oriented channel recess 218. In accordance with a preferred embodiment of the present invention, the recess 118 and the recess 218 have a depth of approximately 80% of the small needle wire 10 diameter. As discussed above, at one end of the recess 118 an alignment abutment 120 is positioned to establish the needle wire 10 position accurately by positioning against the blunt end 24 of the needle wire 10 and the recess 218 similarly includes an alignment abutment 220 positioned to establish needle wire 10 position accurately by positioning against the blunt end 24 of the needle wire 10.

The needle wire 10 is securely and selectively held in the recess 118 or recess 218 by a unique electrically conductive steel top cover member 114, 214. In accordance with the first notch-locating fixture 110, the needle wire 10 is sandwiched between the base 112 and the cover member 114 with clamping pressure afforded by tightening bolts 116 located along the length of the fixture 110. With regard to the second notch-locating fixture 210, the needle wire 10 is sandwiched between the central rod 212 and the cover member 214 with clamping pressure afforded by tightening bolts 216, 217 located at the perimeter of the central rod 212 and the cover member 214.

Unique to the present notch-locating fixtures 110, 210 is a method for maintaining clamping location force and electrical conductivity while not damaging the small needle wire 10. It is important to maintain electrical conductivity between the notch-locating fixtures 110, 210 and the needle wire 10, because when electrical conductivity is not maintained between the notch-locating fixtures 110, 210 and the small needle wire 10, electrical arcing, caused by excessive electrical resistance, damages the part at the point(s) of minimal contact. In accordance with the principles of the present notch-locating fixtures 110, 210, the clamping location force and electrical conductivity is maintained by a thin piece of stainless steel sheet 46 located on top of the small needle wire 10, and between the needle wire 10 and the cover member 114, 214, in contact with the recess 118 of the first notch-locating fixture 110 or the recess 218 of the second notch-locating fixture 210.

A neoprene closed cell foam (or rubber) pad 48 is positioned above the stainless steel sheet 46. The pad 48 is, therefore positioned between the stainless steel sheet 46 and the cover member 114, 214. The pad 48 compresses with the stainless steel sheet 46 when the needle wire 10 is positioned and secured within the recess 118 of the first notch-locating fixture 110 or the recess 218 of the second notch-locating fixture 210. The foam pad 48 maintains distributed compression force, causing the thin stainless steel sheet 46 to be compression formed slightly to the exact configuration of the small needle wire 10 without damaging it. This creates an excellent, full electrical continuity, contact between the needle wire 10 and the notch-locating fixtures 110, 210. The foam pad 48 further holds the needle wire 10 firmly in place and maintains electrically conductive contact.

The top half of the cover members 112, 212 of the first and second notch-locating fixtures 110, 210 has a unique slot 122, 222 to allow the electro-chemical grinding wheel 32 and electrolyte nozzle, located in very close proximity to the wheel, to access the small needle wire 10 located within the sandwich created by the cover member 114 and recess 118 of the first notch-locating fixture 110 and the cover member 214 and the central rod 212 of the second notch-locating fixture 210. The slot 122, 222 width is uniquely sized at a ratio of about 3 times the width of the electro-chemical grinding wheel 32 to allow the electrolyte flow to escape during the cutting operations. Otherwise, the reduced flow causes the notch 12 to be either over cut by the electro-chemical process, or the advancing wheel to physically come in contact with the needle wire part 10, both undesirable events. The notch-locating fixture 110, 210 is in turn located on the table of an electro-chemical grinding apparatus.

It is contemplated the notching fixture may be designed such that it can be easily rotated 180 degrees with the small needle wire parts remaining captured in the sandwich clamp to facilitate producing a second notch opposite the first located precisely 180 degrees on the other side of the needle. This unique feature is afforded by the unique design of the recess in the tool that locates the small needle wire having its outside groove perpendicular side slightly smaller in diameter by 0.2-1% than the actually produced diameter of the small needle wire, allowing the needle to be consistently and precisely located in the tool as a result of the slight interference fit between the small needle wire and the locating recess. This slight amount of interference does not significantly (measurably) affect the location position of the small needle wire notches.

The unique design of the present forming and notching fixtures provide that the small needle wire is predictably and consistently produced during the manufacturing operation by precise repeatable manufacturing controls and statistical process control monitoring. Finally, and with regard to the grinding wheel path, the grinding wheel cannot be traversed across the needle wire as in either conventional grinding or electro-chemical grinding employed on larger parts. By preventing the grinding wheel from traversing across the needle wire as in either conventional grinding or electro-chemical grinding employed on larger parts, the flow of electrical current is controlled to prevent over cutting the small needle wire notch. As such, and in accordance with the present invention, the grinding wheel is perpendicularly plunged into the wire from a contact point ¼ the diameter of the wire off of center. The grinding wheel is then traversed a distance of ½ the diameter of the wire. Finally, the grinding wheel is perpendicularly retracted from the wire at the feed rate determined empirically for the specific needle wire diameter and wheel diameter.

The electro-chemical grinding CBN or diamond impregnated wheel diameter must be a ratio of between 100 to 120 times the diameter of the needle wire to achieve the profile and perpendicularity tolerance specifications stated above using this unique (unorthodox) plunge/traverse/retract path.

Although two notch-locating fixtures are disclosed above, it is contemplated a highly automated rotary fixture would be employed. This rotary fixture would have a series of locating nest details the same as FIGS. 5-8 and FIGS. 14-15 arranged on a circular rotary table wherein a bowl feeder located opposite the ECG wheel would present the already curved needles into the individual nest locations. Then individual covers would close over the needles located in the locating nests to clamp and securely hold the needles. These covers would close as the rotary table turned over a fixed cam lobe, located either underneath or at the perimeter of the rotary table and just before presentation to the ECG wheel. The clamping force would be produced by either a Bellville, compression or torsional spring and an over center mechanism. A second release cam lobe would again be located either underneath or outside the perimeter of the rotary table to release the clamp cover and eject the needle from the locating nest detail after passing the ECG wheel employing the unique (unorthodox) plunge/traverse/retract path producing the notch(s). The rotary table rotational motion and position is controlled by the Computerized Numerical Control (CNC) Electro-Chemical Grinding Machine (ECG).

While the preferred embodiments have been shown and described, it will be understood that there is no intent to limit the invention by such disclosure, but rather, is intended to covet all modifications and alternate constructions falling within the spirit and scope of the invention.

The invention claimed is:

1. A notch-locating fixture for electrochemical grinding in the formation of notches at predetermined locations along a needle wire used in a surgical suturing apparatus, comprising:
    a base including at least one semi-circular recess shaped and dimensioned for receiving and locating the needle wire;
    a cover member including at least one aligned slot formed therein in a manner providing a grinding wheel with access to needle wire held between the base and the cover member;
    a thin piece of a conductive sheet positioned between the needle wire and the cover member; and
    a securing structure selectively coupling the base to the cover member with the conductive sheet positioned therebetween wherein a notch is formed in the wire by electrochemical grinding with the grinding wheel and the conductive sheet.

2. The fixture according to claim 1, wherein the securing structure and clamping force is a plurality of bolts or Bellville, compression, or torsional spring(s).

3. The fixture according to claim 1, wherein the base includes a plurality of semi-circular recesses.

4. The fixture according to claim 3, wherein the plurality of semi-circular recesses includes an alignment abutment shaped and dimensioned for engaging a blunt end of the needle wire.

5. The fixture according to claim 1, wherein the at least one semi-circular recess includes an alignment abutment shaped and dimensioned for engaging a blunt end of the needle wire.

6. The fixture according to claim 1, wherein the recess includes a width which is approximately 5% larger than that of the needle wire diameter and whose radius is also 5% larger than the centerline of the bend radius of the produced needle wire, or 45% of the diameter of the needle wire, measured from the average inside diameter of the needle wire.

7. The fixture according to claim 1, wherein the aligned slot is oriented in a manner creating notches along a side of the needle wire.

8. The fixture according to claim 1, wherein the aligned slot is oriented in a manner creating notches along an exterior circumference of the needle wire.

9. The fixture according to claim 1, wherein the base is a rod.

10. The fixture according to claim 1, wherein the conductive sheet is a stainless steel sheet.

11. The fixture according to claim 1, further including a foam pad positioned between the conductive sheet and the cover member.

12. The fixture according to claim 11, wherein the foam pad is a neoprene closed cell foam pad.

* * * * *